(12) United States Patent
Carver et al.

(10) Patent No.: US 8,114,580 B2
(45) Date of Patent: Feb. 14, 2012

(54) SIMULATION OF NORMAL FRESH BLOOD PLATELETS FOR REFERENCE CONTROL

(75) Inventors: Franklin J. Carver, Benicia, CA (US); Lorraine Granier, San Ramon, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 525 days.

(21) Appl. No.: 12/353,089

(22) Filed: Jan. 13, 2009

(65) Prior Publication Data

US 2010/0178647 A1  Jul. 15, 2010

(51) Int. Cl.
*A01N 1/02* (2006.01)
*G01N 33/96* (2006.01)
*G01N 33/48* (2006.01)

(52) U.S. Cl. .............. 435/2; 436/8; 436/10; 436/17; 436/63; 436/128

(58) Field of Classification Search .................. None
See application file for complete search history.

(56) References Cited

U.S. PATENT DOCUMENTS

| 7,482,161 B2 * | 1/2009 | Carver et al. ............ 436/10 |
| 7,531,357 B2 * | 5/2009 | Carver et al. ............ 436/10 |
| 2006/0223187 A1 * | 10/2006 | Carver et al. ............ 436/10 |

* cited by examiner

*Primary Examiner* — Sandra Saucier
(74) *Attorney, Agent, or Firm* — Kilpatrick Townsend & Stockton LLP

(57) ABSTRACT

The present invention provides for novel analogs of fresh human platelets for use in hematological instrument. Methods for preparing such analogs are also described.

24 Claims, 6 Drawing Sheets

Fresh Blood

Analysis on an Abbott Cell-Dyn CD4000 Hematology Instrument. Upper = scattergram of 90° vs. 7° light scatter with upper and lower limits. Lower = Impedance histogram of frequency vs. size.

Platelet Analog Concentrate Prepared with 210g/L Alpha-Naphtol No Heat, No Glutaraldehyde Analysis on an Abbott Cell-Dyn CD4000 Hematology Instrument. Upper = scattergram of 90° vs. 7° light scatter with upper and lower limits. Lower = Impedance histogram of frequency vs. size.

Platelet Analog Concentrate
Prepared with 210g/L Alpha-Naphtol, Heated 1 Day at 56°C, then Glutaraldehyde Treated Analysis on an Abbott Cell-Dyn CD4000 Hematology Instrument. Upper = scattergram of 90° vs. 7° light scatter with upper and lower limits. Lower = Impedance histogram of frequency vs. size.

Example of U.S. Patent Application Publication No. 2006/0223187.

Platelet Analog Concentrate prepared with 210g/L Alpha-Naphtol then Heated 2 Days at 56°C Analysis on an Abbott Cell-Dyn CD4000 Hematology Instrument. Upper = scattergram of 90° vs. 7° light scatter with upper and lower limits. Lower = Impedance histogram of frequency vs. size.

PIC/POC% Versus Days at 56°C
Effect of 100-500g/L Alpha-Naphtol

Analysis on an Abbott Cell-Dyn CD4000 Hematology Instrument.

Platelet Analog Concentrate Prepared with 450g/L alpha-Naphtol then Heated 3 Days at 56°C Analysis on an Abbott Cell-Dyn CD4000 Hematology Instrument. Upper = scattergram of 90° vs. 7° light scatter with upper and lower limits. Lower = Impedance histogram of frequency vs. size.

SIMULATION OF NORMAL FRESH BLOOD PLATELETS FOR REFERENCE CONTROL

BACKGROUND OF THE INVENTION

This invention resides in the field of reference and control materials for hematology instrumentation, with particular attention to simulated human platelets used as controls for automated platelet counting.

Automated blood cell analyzers that provide cell counts for each of the various types of cells present in a sample of blood do so by measurements of the electrical and/or optical properties of each cell type. These properties include electrical impedance, electrical conductance, radio frequency modulation, light scattering, and light absorption, in various combinations. A variety of analyzers are commercially available and used in clinical laboratories, individual analyzers differing in the manner in which they collect and process the data.

Federal regulations require that blood cell analyzers be checked regularly against controls to verify the reliability of the analyzers. The controls are synthetic suspensions that have the certain physical and chemical characteristics similar to those of blood and that include stable cells or particles whose sizes and shapes closely approximate those of the different cells present in human blood. Unfortunately, the different methodologies among the various instruments react to controls in different ways, and certain types of control particles that serve as effective substitutes for one kind of cell on a particular instrument have been found to appear like another type or even like cell debris on a different instrument.

Among the various types of cells in human blood that must be represented in a control, platelets are particularly problematic. The use of actual platelets in the control is unfavorable since platelets disintegrate when the blood in which they are suspended escapes from the vascular system, and the disintegration causes the liberation of thromboplastins that cause blood clotting. In addition, platelets are easily activated and tend to aggregate. They are also expensive. For these reasons, simulated platelets have been developed that are less costly and that lack these unfavorable characteristics. Simulated platelets are typically biological cells or non-biological particles. When biological cells are used, they are cells other than platelets that have been modified to bear characteristics that render them detectable by the same parameters as actual platelets and thereby distinguishable from other cell types. When particles are used, they are particles that have these characteristics. The characteristics differ depending on the methodology of the detection. In some cases, the distinguishing characteristics are size range and size distribution, while in others, the chemical contents, such as a lack of hemoglobin as compared to the presence of hemoglobin in a red blood cell, serve as the differentiating characteristics. For a control to be useful in different types of instruments rather than only one, it is important that the simulated platelet component be detectable as platelets regardless of the methodology of the instrument. This, unfortunately, is not always the case, even when the measured characteristic is size distribution, i.e., it is not uncommon for a particular control to be read as having one size distribution by one means of detection and another by a different means of detection. Fresh human platelets have a log-normal size distribution rather than a Gaussian distribution, and detection instrumentation that relies on particle size also must have either controls that have a log-normal distribution or a computer algorithm that can accept a population that approaches a log-normal size distribution.

A relatively inexpensive substitute for actual human platelets and one that lacks the disintegration and aggregation characteristics of human platelets are red blood cells from non-human vertebrates. To render these cells useful as simulated platelets, the cells are reduced in size and treated with a fixing agent to toughen the cell membranes. Goats are a favored source of red blood cells as substitutes for platelets, since goat red blood cells can either be altered or blended to a size and size distribution similar to those of human platelets. One method of size adjustment is the suspension of the cells in a hyperosmotic solution to draw cellular fluid from the cells by osmotic pressure. The fixing treatment is performed either before or after the use of osmotic pressure, depending on whether the fixing treatment is used as a means of controlling or limiting the rate of passage of cellular fluid when osmotic pressure is applied.

When the fixing treatment is done to control the rate of fluid passage through the cell membrane, the purpose is to achieve a desired particle size range and size distribution. Achieving a particular particle size range and distribution as measured by optical techniques however does not always result in the same size range and distribution as measured by electrical techniques. One method of correcting this deficiency is disclosed by Ryan, W. L. (Streck Laboratories, Inc.), U.S. Pat. No. 5,008,201, issued Apr. 16, 2001. This method involves preparing a graduated series of particle sizes by subjecting different populations of cells to different degrees of fixation to cause each population to shrink to a different degree when osmotic pressure is applied. The populations are then combined in proportions that will collectively approximate the desired size distribution. This is labor-intensive and susceptible to flag in both the selected proportions and the differing degrees of treatment.

It has been discovered that platelet analogs with a size range and distribution detected by optical measurement that conform closely to the size range and distribution detected by electrical measurement can be prepared from red blood cells of a non-human vertebrate animal that have already been shrunken in size and then fixed. The preparation method involves first heating the size-reduced and fixed cells to a temperature above ambient temperature for a period of time sufficient to have a denaturing effect on the cells, then exposing the cells to a fixing agent, preferably before or after cooling the cells to a temperature at or close to ambient temperature. Effective results with this method can be achieved without the need for separately preparing distinct lots of cells of different sizes and combining the lots in carefully selected proportions to achieve a combination that approximates the desired size distribution. The process can instead be performed on a single lot and still achieve the desired distribution as detected by both electrical and optical modes of measurement. This preparation method brings the size and distribution characteristics closer to those that enable the shrunken cells to be used as controls for evaluating actual human platelets.

U.S. Pat. No. 4,179,398 and U.S. Patent Application Publication No. 2006/0223187 describe methods for preparing human platelet analogs using goat red blood cells as starting material. The present invention provides a new process for producing simulated human platelets of more desirable characteristics, such as improved optical properties and a more consistent reading in size range and distribution between optical and electrical measurements.

BRIEF SUMMARY OF THE INVENTION

In one aspect, the present invention relates to a process for the manufacture of human platelet analogs for use as reference controls in automated blood cell analyzers. The claimed process includes these steps: (a) shrinking red blood cells of a non-human vertebrate to the size of human platelets by extraction of cellular fluid from the red blood cells; and (b) heating the cells from step (a) at a temperature of at least 50° C. for a time period of at least 1 day.

In some embodiments, step (a) of the process further includes heating the cells, after the shrinking of the cells, at a temperature of about 40° C. for about 0.5 to about 5 hours, such as for about 3 hours. In other embodiments, step (b) of the process is performed in the presence of a denaturing agent; or step (b) may further comprises treating the cells from step (a) with a denaturing agent for at least 2 hours and then removing the denaturing agent from the cells prior to the heating in step (b).

In some embodiments, the claimed process further includes step (c) of fixing the cells from step (b) with a fixing agent. An exemplary fixing agent is glutaraldehyde. In other embodiments, the red blood cells are goat red blood cells.

In some embodiments, the heating in step (b) is performed at about 50° C. to about 75° C., e.g., at about 56° C. In some embodiments, the heating time period in step (b) is at least 2 days, 3 days, 4 days, 7 days, 14 days, or 21 days. In other embodiments, the denaturing agent is α-naphthol, and the concentration for which may range from about 100 g/L to about 500 g/L, or at least 400 g/L, or at least 500 g/L.

In some embodiments, the heating time period is at least 7 days and α-naphthol concentration is at least 400 g/L; or the heating time period is at least 14 days and α-naphthol concentration is at least 400 g/L; or the heating time period is at least 21 days and α-naphthol concentration is at least 400 g/L; or the heating time period is about 21 days and α-naphthol concentration is about 500 g/L.

In a second aspect, the present invention relates to modified red blood cells for use as reference controls in automated blood cell analyzers prepared by any one of the processes described in the above paragraphs and especially by any one of claims 1-25.

DETAILED DESCRIPTION OF THE INVENTION

I. Introduction

Figure 1:
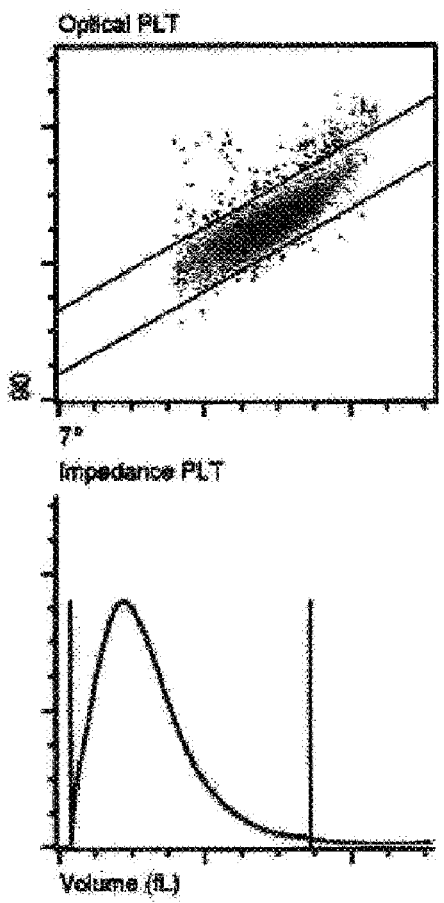
FIG. 1: analysis of fresh blood on an Abbott Cell-Dyn CD4000 hematology instrument.

The present inventors discovered that modification of conventional methods for producing platelet analogs, such as non-human red blood cells shrunken to a desired size and preferably fixed, by heating the red blood cells at an elevated temperature for an extended period of time in combination with the use of a denaturing agent (such as α-naphthol), can improve the optical quality of the analogs such that consistent reading between optical and electrical means can be achieved, making the analogs better controls for use in hematological instruments.

II. Starting Material

The starting material for the composition of the present invention may be whole blood from a non-human vertebrae, such as a goat or any of the common species of goat. There is no concern about any specific antigen or group of antigens, such as the hepatitis-associated antigens that are occasionally present in human platelet compositions, so no precautions therefor are necessary. The volume and size distribution range of goat erythrocytes vary to some extent with the age, sex, hereditary factors, breeding history, metabolic status, and the manner and environment in which the goat was raised. In general, however, goat erythrocytes have a mean erythrocyte volume that is two to three times the mean platelet volume of human platelets, normally about 4.1 microns in diameter and about 35 cubic microns in volume.

III. Precipitation Step

The red blood cells from whole blood of a non-human vertebrate animal, e.g., a goat, are preferentially precipitated, that is, caused to settle out at a faster rate than the remainder of the blood cell components, by various methods known in the art, for instance, by mixing the blood with a solution comprising a polymerized sugar, a salt of a dicarboxylic acid, and a weak base, or by a centrifugation method.

As an example, the polymerized sugar is polymerized anhydroglucose, or, as it is commonly known in the art, Dextran, with a molecular weight of from about 100,000 to about 500,000, or a molecular weight of from about 150,000 to about 200,000. Another possible polymerized sugar is polymerized sucrose of 500,000 molecular weight. The concentration of the polymerized sugar can be from about 20 to about 50 grams per liter, for example, about 30 grams per liter.

The salt of a dicarboxylic acid may be any of the common salts such as the alkali metal salts, while the dicarboxylic acid may be any such acid which is effective in assisting precipitation of the red blood cells. For example, the acid is oxalic acid or tartaric acid. The di-alkali metal salt of tartaric acid is often used since it tends to impart a spherical shape to the cells.

The weak base may be any common weak base such as ammonia, mono- or di-basic alkali metal phosphates or bicarbonates. For example, the weak base is sodium bicarbonate.

The salt of the dicarboxylic acid and the weak base should be in sufficient concentrations to impart to the precipitating solution a pH range of from about 6.0 to about 8.5, most preferably from about 6.5 to about 7.5. It has been discovered that the precipitation step is inversely pH dependent; that is, the lower the pH, the greater the precipitation rate.

Various methods of centrifugation are also effective and convenient means for precipitating red blood cells from a whole blood sample of a non-human vertebrate animal. A number of centrifugation equipment and established protocols are commercially available for this particular purpose.

It should be understood that there are many variations possible in the types and concentrations of the components of the precipitating solution set forth above which will suggest themselves to one of ordinary skill in the art, the only limitations being those of preventing undue red blood cell association and hemolysis.

IV. Shrinking Step

The red blood cells precipitated in the precipitation step are drawn off and shrunk by suspending them in a series of aqueous hypertonic salt solutions. Since the principle of a cell shrinking in a hypertonic solution, or one in which the concentration of solutes is greater than the concentration of solutes in the cell, is a simple one, it is envisioned that any salt will do as the solute in this step of the invention, so long as it does not cause undue hemolysis or cell association. Addition of a reagent that has a dispersing effect is desirable, since it helps to prevent undue cell association. Suitable dispersing agents are the di-alkali metal salts of the naphthol-disulfonic acids, and the low molecular weight (less than 42,000) dextrans. The artisan will also recognize some potential limitations as to choice of salt if the composition of the invention is to be used in electrical platelet counters, giving due regard to the relative conductivity/resistance of the liquid suspension and any possible adverse electrolytic effects.

An especially suitable class of salts for the shrinking step because of their dual role as a dispersing agent and a shrinking agent are the di-alkali metal salts of the naphthol-disulfonic acids, such as the dipotassium salt of 2-Naphthol-6,8 disulfonic acid and the disodium salt of 2-Naphthol-3,6 disulfonic acid.

The precipitated red blood cells (e.g., goat red blood cells) are shrunken by successively suspending them in aqueous solutions of the salt in successively increasing concentrations until the desired size range is achieved. Since human blood cell platelets are in the range of from about 1.8 to about 3.6 microns in diameter and have a volume from about 5 to about 25 cubic microns, this is the desired range of sizes. The normal platelet count in humans is from about 200,000 to about 400,000 per cubic millimeter, while low counts are as little as 75,000 per cubic millimeter. Thus, the desired cell population or density is from about 75,000 to about 400,000 cells per cubic millimeter. At all times it is important to maintain the concentration of the salt solution equal to or greater than the concentration of the next preceding solution so as to maintain hypertonicity and prevent any swelling of the cells.

The effective final concentration of the salt of the hypertonic solution should be in the range of from about 650 to about 700 milliequivalents, preferably about 680, per liter. This may be achieved in any number of additions of incremental concentrations, the only limitations being the practical ones of time and keeping the salt in solution without precipitation. In connection with the latter problem, it has been found especially useful to use equal portions of the dipotassium and disodium salts of naptholdisulfonic acids.

In a preferred embodiment of the invention the cells are successively suspended in three aqueous hypertonic solutions of successively greater concentrations, the first one ranging in concentration from about 100 to about 300 milliequivalents per liter, preferably 200 milliequivalents per liter, the second one being double the concentration of the first one, and the third being double the concentration of the second. By adding three volumes of the hypertonic solution each time to the remaining preceding suspension, the effective final concentration is in the preferred range. After each suspension, the cells will precipitate and the supernatant should be discarded. The shrinking process may be accelerated considerably by centrifugation after each suspension. A suitable range of speeds and times for centrifugation is from 1,000 to 3,000.times.g for about 10-20, preferably 15 minutes for each step. When the cells have shrunken to the desired size, they can be resuspended in a fresh solution of the same concentration as the last shrinking solution, in preparation for the optional fixing step or directly for the denaturing step.

Methods of preparing goat erythrocytes to bring them into the size range of human platelets are known in the art. Included among these methods are the extraction of controlled amounts of cellular fluid from the erythrocytes by osmotic pressure as indicated above, in conjunction with fixation of the cell membrane with the use of fixing agents, likewise as indicated above. Additional treatments and treatment agents are used in some cases as well, including anticoagulants and stabilizers, for example, and the application of heat in some cases to anneal cells after the extraction of cellular fluid. All of these treatments, however combined and in whatever order, prepare the erythrocytes for the processing steps that constitute the present invention. The size range of the erythrocytes prior to processing in accordance with the invention, expressed herein by the term "mean platelet volume" despite the fact that the erythrocytes are platelet analogs rather than true platelets, can vary. In most cases, best results will be achieved with a size range of from about 5 femtoliters to about 15 femtoliters, preferably from about 5 femtoliters to about 10 femtoliters, and most preferably from about 7 femtoliters to about 9 femtoliters.

Optionally, an additional step of brief heating may be performed following the shrinking of the red blood cells. Specifically, the shrunken cells are placed in an environment having a temperature moderately raised from the room temperature (for example, at 40° C.) for a relatively short duration of time (for example, somewhere between 0.5 to 5 hours, such as 3 hours). This step serves the purpose of re-annealing of the cell membrane.

V. Denaturing Step

According to this invention, the pre-treated red blood cells (i.e., red blood cells that have been shrunken and optionally briefly heated, e.g., at 40° C. for 3 hours) are then denatured by heating for an extended time period to further improve their optic properties and make a better "fit" for the optic channels during measurement.

The denaturing step in the practice of the invention comprises the heating of the size-reduced erythrocytes to a sufficient temperature and for a sufficient period of time to achieve a denaturing effect, either at the presence of or at the absence of a denaturing agent (e.g., α-naphthol). This thermal treatment is of sufficient degree and duration to achieve this effect without damage to or coagulation of the cells. The temperature may vary with the length of time the cells are held at the temperature. In most cases, the most efficient results in terms of treatment time will be obtained by heating to a temperature of about 50° C. or higher, preferably from about 50° C. to about 75° C., and most preferably from about 50° C. to about 60° C. The sufficient duration of heating treatment can vary depending upon factors including the temperature and the presence and concentration of a denaturing agent that the cells have been treated with. For instance, when a higher temperature or a higher concentration of a denaturing agent such as α-naphthol is used, the same denaturing effect can be achieved even if a shorter time period of heating is applied. As used in this application, any chemical that can achieve the desired denaturing effect or can enhance the denaturing effect of heating can be used as a denaturing agent. In some exemplary embodiments, a denaturing agent useful for this invention is a naphthol or naphthol derivative having formula (I) or (II) as provided below.

As described in the examples in a later section, pre-treated red blood cells (also referred to as the re-annealed membranes) that have already been shrunken to a desirable size (and then preferably treated by brief moderate heating) are subsequently heated at an elevated temperature for a time period sufficient to denature the cellular proteins and to improve the optic properties of the cells, especially to achieve a high level of consistency between readings in size range/distribution by optical measurement and by electrical impedance, so as to reduce or eliminate flag signals on an automated hematological instrument, e.g., the PIC-POC flags on the Abbott Cell-Dyn 4000 Hematology Instrument, which indicates a greater than 20% discrepancy between the impedance system count (PIC) and the optical system count (POC). The elevated temperature is usually between 50-75° C., e.g., 56° C. The time period for heating is usually at least 24 hours and can be at least 48, 72, 96, 120, 168, 336, or 504 hours. In some cases, heating can be performed for an even longer period. The heating step is carried out in an environment of a constant temperature, such as a water bath.

This process of modifying non-human red blood cells can be performed in some cases in the presence of a denaturing agent to further enhance the effect of heating or to achieve the same denaturing effect for a shorter time period of heating. For instance, naphthols, including α-naphthol and β-naphthol, can serve as denaturing agents. Other naphthol derivatives are also useful for as denaturing agents in this process. These naphthol derivatives have formula (I) or (II):

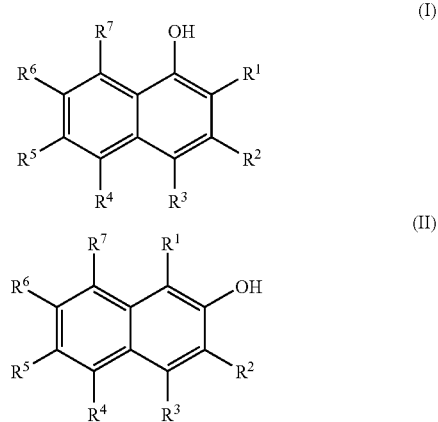

wherein $R^1$, $R^2$, $R^3$, $R^4$, $R^5$, $R^6$ and $R^7$ are each independently selected from —H, alkyl, aryl, alkoxy, —OH, —$NH_2$, alkyl-NH—, aryl-NH—, halogen, sulfo, —C(O)H, alkyl-C(O)—, alkyl-$SO_2$NH—, aryl-$SO_2$NH—, —$NO_2$, —NO, —COOH, —COO-alkyl, —CN or —C(O)NH-alkyl. In some embodiments of the alpha-naphthol derivatives of formula (I), $R^1$, $R^2$ and $R^3$ are each independently selected from alkyl, aryl, —OH, —$NH_2$, alkylNH—, halogen, sulfo, —C(O)H, alkyl-C(O)—, —$NO_2$, —NO, —COOH or —COO-alkyl. In certain instances, $R^4$, $R^5$, $R^6$ and $R^7$ are each independently —H, —OH, —$NH_2$, sulfo, halogen, —CN, —COOH or —COO-alkyl. In other embodiments of the alpha-naphthol derivatives of formula (I), $R^1$, $R^2$, $R^3$, $R^4$, $R^5$, $R^6$ and $R^7$ are each independently selected from —OH, —$NH_2$, —Ph, —$SO_3$H, —Br, —Cl, —F, —C(O)H, —C(O)$CH_3$, —$NO_2$, —NO, —COOH, —C(O)OCH$_3R^1$, —$SO_2$NH-alkyl, —OCH$_3$, —CN, —C(O)NH-alkyl, —C(O)NH-aryl, alkyl-NH— or aryl-NH—. In certain instances, $R^1$, $R^2$ and $R^3$ are each independently selected from —OH, —$NH_2$, —Ph, —$SO_3$H, —Br, —Cl, —F, —C(O)H, —C(O)$CH_3$, —$NO_2$, —NO, —COOH or —C(O)OCH$_3$. In one occurrence, $R^1$, $R^2$, $R^3$, $R^4$, $R^5$, $R^6$ and $R^7$ are —F.

Examples of commercially available α-naphthol derivatives that can be used in the present invention include, but are not limited to, 4-chloro-1-naphthol, 1,5-dihydroxynaphthalene, 1,7-dihydroxynaphthalene, 1-methoxy-4-nitronaphthalene, 4-Fluorosulfonyl-1-hydroxy-2-naphthoic acid, 1,3-Dihydroxynaphthalene, 4-methoxy-1-naphthonitrile, 2-nitro-1-naphthol, 4-methoxy-1-naphthol, 2-acetyl-1-naphthol, 9-phenanthrol, 1-naphthol-3,6-disulfonic acid disodium salt hydrate, alpha-hydroxy-heptafluoronaphthalene, 5-amino-1-naphthol, N-(2-Acetamidophenethyl)-1-hydroxy-2-naphthamide, 8-Amino-1-naphthol-3,6-disulfonic acid or monosodium salt monohydrate thereof, 8-Amino-1-naphthol-5-sulfonic acid, chromotropic acid or salt thereof, 2,4-dichloro-1-naphthol, 1-naphthol-2-sulfonic acid or potassium salt thereof, 1-Naphthol-4-sulfonic acid or salt thereof, 1,7-dihydroxynaphthalene, 4-Aminosulfonyl-1-hydroxy-2-naphthoic acid, 5-hydroxy-1-naphthalenesulfonamide, 6-amino-1-naphthol, 2-(2-Hydroxy-1,1,1,3,3,3-hexafluoropropyl)-1-naphthol, 1,4-dihydroxy-2-naphthoic acid, 1,4-Dihydroxy-2-naphthoic acid phenyl ester, 1,6-dihydroxynaphthalene, 4-hydroxy-1-naphthaldehyde, 7-Anilino-1-naphthol-3-sulfonic Acid, 6-amino-1-naphthol-3-sulfonic acid, 4-nitro-1-naphthol, 4-hydroxy-6,7-di(methoxycarbonyl)-1-naphthol, 2,4,6,8-tetranitro-5-hydroxy-1-naphthol, 4,6-dinitroso-5-hydroxy-1-naphthol, 4,6-diamino-5-hydroxy-1-naphthol, 2,2'-binaphthyl-1,1'-diol, 2,3-di(methoxycarbonyl)-1-naphthol, 2-acetyl-3-butyl 1-naphthol, 3-phenyl-1-naphthol, 1-naphthol-8-sulfonic acid or salt thereof, 3-chloro-1,4-dihydroxynaphthalene, 1-Amino-5-naphthol-7-sulfonic acid, 2-fluoro-1-naphthol, 3,5-Dihydroxy-2-naphthoic acid, 1-Naphthol-3-sulfonic acid or salt thereof, 2,4-dibromo-1-naphthol, 6-amino-1-naphthol, 2-Amino-1-naphtholhydrochloride, 2,3-dicyano-1,4-dihydroxy-5-nitronaphthalene, 1,2-Dihydroxynaphthalene, 1-Hydroxy-2-naphthaldehyde, 4-phenylsulfonamido-1-naphthol, 2-(4-phenylsulfonyl)-4-(4-chlorophenylsulfonamido)1-naphthol and 4-acetamido-1-naphthol.

The concentration of the denaturing agent can vary depending on the nature of the agent as well as the duration and the temperature used in the heating step. Typically, the concentration ranges from about 100 g/L to about 500 g/L.

In the alternative, the shrunken red blood cells may be treated with a denaturing agent (such as α-naphthol) for a sufficient amount of time (e.g., at least two hours) without heating (e.g., at room temperature). After the denaturing agent is removed, the cells are then subject to the heating treatment as described above, for instance, at an elevated temperature between 50-75° C., e.g., 56° C., for a time period of at least 24 hours, in some cases at least 48, 72, 96, 120, 168, 336, or 504 hours, or for an even longer duration. In this treatment scheme, the denaturing agent's concentration also ranges from about 100 g/L to about 500 g/L.

VI. Fixing Step

Fixing of the shrunken and denatured/heated red blood cells is an optional step in this invention. In other words, the red blood cells treated by a process described above can, according to the present invention, be directly used as platelet analogs in a hematological instrument without the fixation step by a fixing agent. Optionally, the red blood cells obtained following the shrinking and denaturing/heating steps are further treated with a fixing agent such as glutaraldehyde to toughen the cell membranes and to prevent their biodegradation. As such, any chemical that can achieve this effect can be used as a fixing agent for the method. For example, fixing of pre-treated red blood cells is accomplished by contacting the suspension of the cells with a solution of an organic aldehyde such as formaldehyde or glutaraldehyde. The aldehyde may be added in concentrations anywhere from about 5% to about 50% by weight, so long as the final concentration thereof is in the range of from about 0.5% to about 1.0%, preferably about 0.6% by weight. As is the case with the precipitating and shrinking solutions, the only practical limitations on selection of an appropriate fixing agent (e.g., aldehyde) and concentration thereof are elimination of undue cell association and hemolysis and potential undesirable electrolytic effects.

In one embodiment, glutaraldehyde in concentrations below 50% by weight is dripped slowly into the hypertonic suspension of cells while the same is rapidly stirred. Since the addition of the fixing solution dilutes the hypertonic suspension, sufficient amounts of the hypertonic shrinking solution should be added to maintain the concentration thereof at the same level and so maintain the size of the shrunken cells.

The fixed cells are thereafter allowed to settle out, separated, washed with a buffered solution, and placed in a storage solution.

As an optional step prior to recovering the shrunken cells, in order to assure a high-quality product containing only the hardiest cells with a stabilized cell population, the cell suspension may be subjected to severe agitation by any appropriate means, such as sonic agitation. This step tends to destroy the weaker-membraned cells and thus leave the more hardy for use as a platelet-counting reference control.

The buffered washing solution should be neutral to alkaline, preferably in the pH range of from about 7.0 to about 10.0. Although any buffered solution may be used, with due regard to the problems of hemolysis, cell association and electrolytic effects noted above, a preferred set of buffering reagents includes sodium hydroxide, sodium bicarbonate, and sodium chloride. The shrunken cells should be washed with the buffered solution as many times as is necessary to obtain a clear supernatant, preferably at least three times.

The storage solution in which the cells are suspended may be virtually any fluid, including mere water, which does not have a deleterious effect on the fixed cells, such as causing hemolysis, cell association or biodegradation. A preferred storage solution is basically the same buffered solution used in the washing step with the addition of a bacteriocidal or bacteriostatic agent to prevent contamination and a dispersing agent. The bacteriocidal or bacteriostatic agent can be any known agent added in sufficient concentration to reduce or check bacterial growth. An inexpensive and preferred bacteriocidal/bacteriostatic agent is gentamicin and/or Proclin 150. Another is the hydrochloride salt of tetracycline. Each may be added in a concentration of about 0.1 grams per liter. The dispersing agent may be one dialkali metal salt of a naphthol-sulfonic acid or a low molecular weight dextran. A preferred dispersing agent is dextran with a molecular weight of about 20,000 to about 41,000, preferably about 40,000, added in a concentration of about 30 grams per liter. If a di-alkali metal salt of a naphthol-sulfonic acid is used, such as the dipotassium salt of 2-Naphthol 6,8-disulfonic acid, the preferred concentration is from about 0.02 to about 0.05, preferably about 0.04 molar.

If the platelet reference control is to be used in connection with electronic platelet counting devices, it preferably has an electrolyte in the storage fluid in order to facilitate electrical conductivity. However, the pH of the solution in such applications should be substantially neutral to alkaline and a buffering system which may double as an electrolyte is advantageously used to maintain the pH of the solution.

The cell population or density may be adjusted by any known dilution or concentration technique. For example, if the product shows a density of 300,000 cells per cubic millimeter, and the desired density is about 75,000, the fluid suspension should be diluted by adding three volumes of diluent to obtain the desired density.

In executing all of the above steps in order to assure high purity of product, it is preferable to use reagent grade chemicals, as opposed to technical grade. It is also preferable to take precautions against the cells sticking to glassware, which they have a natural tendency to do. A standard measure to accomplish this is to "siliconize" all glassware to be used by coating it with a solution of tetramethyl silane in benzene, and subjecting the coating glassware to 100° C. (dry air) for 15 to 30 minutes.

VII. Formulating Step

Following shrinking step, the denaturing/heating step, and the optional fixing step, the red blood cells can be suspended in any of a variety of fluids, including hypo-osmotic, iso-osmotic, or hyper-osmotic fluids. Iso-osmotic aqueous liquids, i.e., those that do not form an osmotic pressure differential across the membranes of the cells, are preferred since they are most compatible with the final blood control product. Conventional additives can be added for the same purposes that they serve in standard cell suspensions of the prior art. Propylene glycol, for example, can be added to optionally clear the cytoplasm and to reduce cell-to-cell binding.

In certain embodiments of the invention, the cells are preconditioned prior to the heating and fixation steps of the present invention. Pre-conditioning is achieved by moderate heating for at least an hour to a temperature below the temperature ranges cited above, preferably in diluted form with an iso-osmotic diluent, a saline diluent, or water, and in some cases, with dissolved propylene glycol in any of these media. The preferred temperature range for pre-conditioning is from about 30° C. to about 40° C., and the pre-conditioning time is from about 2 hours to about 4 hours. Pre-conditioning tends to improve the agreement between the optical and electrical methods of platelet counting.

Still further improvements in the agreement between the optical and electrical methods of platelet counting are achieved by incubating the cells in a suspension of human red blood cells in addition to the various treatment steps discussed above. This incubation is preferably performed at room temperature for a period of at least one day, more preferably for at least 5 days, and most preferably for at least 10 days.

EXAMPLES

The following examples are provided by way of illustration only and not by way of limitation. Those of skill in the art will readily recognize a variety of non-critical parameters that could be changed or modified to yield essentially the same or similar results.

Example 1

Heating of Pre-Treated Red Blood Cells

Figure 2:
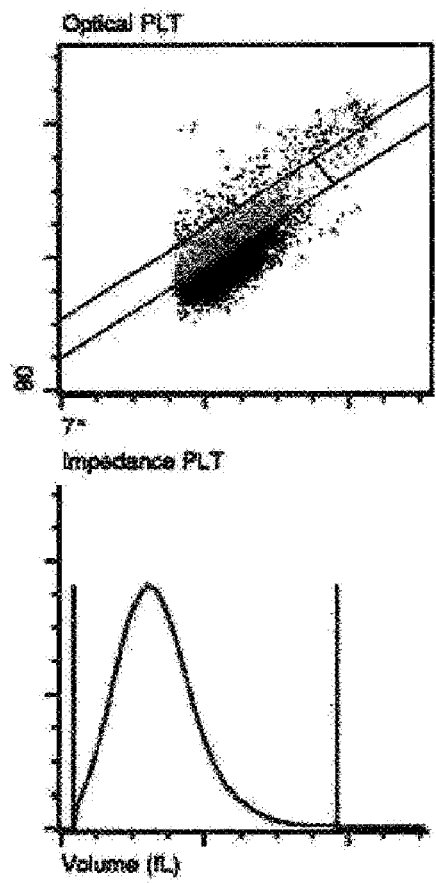
FIG. 2: analysis of platelet analog concentrate prepared with 210 g/L α-Naphthol (no heat, no glutaraldehyde) on an Abbott Cell-Dyn CD4000 hematology instrument.
Figure 3:
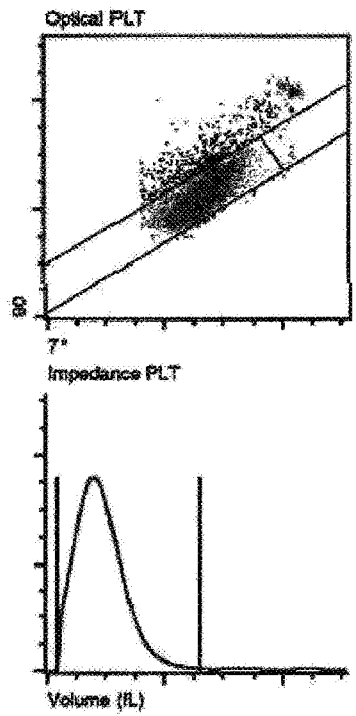
FIG. 3: analysis of platelet analog concentrate prepared with 210 g/L α-Naphthol (heated 1 day at 56° C., then glutaraldehyde-treated) on an Abbott Cell-Dyn CD4000 hematology instrument.

Compared to fresh blood (FIG. 1) an experimental blood control formulation for Abbott CD4000 and Sapphire instruments ("Hem-Au" hereafter) with current re-annealed membranes has excellent platelet impedance counting precision but poor optical counting precision (FIG. 2). The mean impedance count is typically high when compared to the optical count resulting in a high occurrence of the PIC/POC flag; this flag is set when the mean impedance count (PIC) is substantially different from the platelet optical count (POC). The current re-annealed membranes being used do not fit correctly into the optical channel of the CD4000 and Sapphire Hematology Instruments. In the past studies and a pending patent application (FIG. 3: U.S. Patent Application Publication No. 2006/0223187), it is shown that treating the finished re-annealed membranes with glutaraldehyde and heat 56° C. for 24 hours will make re-annealed membranes "fit" better into the optical platelet channel on the CD4000. This patent-pending process allows for platelet analogs with excellent platelet impedance counting (PIC) precision and excellent platelet optical counting (POC) precision. However, the Abbott CD4000 instrument will give multiple PIC/POC patient flags to indicate that the platelet analogs are not evaluated the same as fresh blood. In addition, free aldehyde groups associated with the platelet analogs will interfere with the fluorescence on the WBC channel of the CD4000. This example demonstrates that extended denature heating alone will change the shape of the finished re-annealed membranes and thus help them "fit" into the optical platelet channel better. Once the platelets fit better, the occurrence of the PIC/POC flag will be less.

Materials:
  Re-Annealed Membranes;
  Processed human red blood cells in a compatible media used to formulate a blood control;
  A hypo-osmotic saline as Frog Ringers with an organic buffer (i.e., modified or M-Ringers);
  Suspending media used as a diluent in the formulation of a blood control;
  1 mL sterile pipets;
  15-ml centrifuge tube;
  2.5-ml vials and caps;
  Abbott CD1700, CD3500, and CD4000 Hematology Analyzer;
  Water bath.

Methods:
1. Heating the Re-Annealed Membranes (4 days at 56° C.)
   a. 10 mls of Re-Annealed Membranes were poured into 1×15 ml centrifuge tubes.
   b. Place the tube in the water bath at 56° C.
2. Wash the heated Re-Annealed Membranes
   a. Remove the heated Re-Annealed Membranes.
   b. Centrifuge the tube for 15 minutes at full speed (3600 rpm).
   c. Aspirate and discard the supernatant.
   d. Fill the tube to the 14-ml mark with Ringers.
   e. Repeat steps 2.b. through 2.d. three more times.
   f. Re-suspend in M-Ringers to an approximate count of $25.9 \times 10^6$.
3. Formulate samples
   a. Concentrate the processed human red blood cells to a normal count ~$4.50 \times 10^6$.
   b. Manufacture a low, normal, and high platelet sample using the human red blood cells.
   c. Run precision studies on the CD4000 on all three levels.
   d. Run additional samples on the CD1700 and CD3500.
   e. Store the samples at 2-8° C.
4. Results
   The heated re-annealed membranes fit perfectly into the optical platelet channel on the CD4000. When they were added to the processed human red blood cells at low and normal platelet concentrations, there were no PIC/POC flags.
   The CV % on all three levels of the PLTo and PLTi were within the precision limits of the Cell-Dyn 4000.
   There were no platelet, white blood cell, or red blood cell flags when samples were run on the CD4000. Samples worked on other impedance counters as the Abbott CD1700 and CD3500.

Example 2

Effect of Naphthol on Goat Red Blood Cells Prior to Heating

Purpose:
  To determine if the amount of α-Naphthol used in processing blood cells is inversely related to the amount of time required to heat the α-Naphthol treated cells at 56° C. in order to eliminate the PIC/POC flag on the Abbott CD4000 Instrument.

Equipment:
  Abbott CD4000 Hematology Analyzer, S/N 30380AA
  VWR Water Bath, Model 89032-218, S/N WL0713029
  VWR Centrifuge, Clinical 50, S/N F703069, Calibrated on Oct. 15, 2007

Materials:
  Goat red blood cells
  Deionized water for preparing Naphthol solution
  Processed human red blood cells in a red blood cell suspending media used to formulate a blood control
  Reagent Gluteraldehyde—pH 7.00
  Frog Ringers with an organic buffer
  0.9% NaCl (Iso-osmotic saline)
  Suspending media used as a diluent in the formulation of a blood control
  125-mL glass bottle and cap
  1 mL sterile pipets
  15-mL centrifuge tubes
  2.5-mL vials and caps Procedure:
Re-Annealed Membranes
  1) Gently lyse the goat red blood cells in a hypotonic environment.
  2) Anneal the membranes at about 40° C. for about 3 hours.
  3) Suspend in 100, 200, 300, 400, or 500 g/Liter α-Naphthol for 2 hours.
  4) Perform a 0.3% glutaraldehyde stabilization.
  5) Wash in an iso-osmotic balanced saline solution.

Heating the Re-Annealed Membranes
  1) 75 mls each [1-series (100 g/L), 2-series (200 g/L-stock), 3-series (300 g/L), 4-series (400 g/L, and 5-series (500 g/L)] of the Re-Annealed Membranes were poured into sterile 125-ml glass bottles, and placed in a water bath at 56° C.
  2) Mix bottles after 30 minutes to resuspend the platelets and evenly disperse the heat.
  3) Remove samples (see Table I).

TABLE I

| Experiment Number | Concentration of α-Naphthol | Time at 56° C. |
|---|---|---|
| 1a | 100 g/L | 24 hrs. |
| 1b |  | 48 hrs |
| 1c |  | 72 hrs |
| 1d |  | 168 hrs |
| 1e |  | 336 hrs |
| 1f |  | 504 hrs |
| 2a | 200 g/L | 24 hrs |
| 2b |  | 48 hrs |
| 2c |  | 72 hrs |
| 2d |  | 168 hrs |

TABLE I-continued

| Experiment Number | Concentration of α-Naphthol | Time at 56° C. |
|---|---|---|
| 2e | | 336 hrs |
| 2f | | 504 hrs |
| 3a | 300 g/L | 24 hrs |
| 3b | | 48 hrs |
| 3c | | 72 hrs |
| 3d | | 168 hrs |
| 3e | | 336 hrs |
| 3f | | 504 hrs |
| 4a | 400 g/L | 24 hrs |
| 4b | | 48 hrs |
| 4c | | 72 hrs |
| 4d | | 168 hrs |
| 4e | | 336 hrs |
| 4f | | 504 hrs |
| 5a | 500 g/L | 24 hrs |
| 5b | | 48 hrs |
| 5c | | 72 hrs |
| 5d | | 168 hrs |
| 5e | | 336 hrs |
| 5f | | 504 hrs |

Wash the 24-hour to 504-hour Heated Re-Annealed Membranes
1) Add a 2 mL sample to a 15 mL tube.
2) Fill the centrifuge tube to 14.5 mL with M-Ringers and resuspend.
3) Centrifuge the tube for 15-minutes at 3600 rpm.
4) Aspirate and discard the supernatant.
5) Repeat washing three more times.
6) Fill the tube with Suspending Media and resuspend the particles.
7) Centrifuge the tube for 10-minutes at 3600 rpm.
8) Wash two more times and adjust to a count of 20-30×$10^6$.

Formulate a Sample
1) Add the heated/washed platelets to the human RBC component to an approximate normal platelet count (~250×$10^3$).
2) Run on the CD4000.

Results:
An increase in the concentration of α-Naphthol is needed to produce platelet analogs that do not recover PIC/POC flags when run on the CD4000.

The change in the concentration of α-Naphthol changes the optical properties of the platelet analogs such that the Cell-Dyn 4000 is capable of equally counting the platelets optically and by the impedance method.

The higher the concentration of α-Naphthol used, the smaller the MPV.

The longer the platelet analogs are heated, the smaller the MPV. It is more beneficial to not heat the platelet analogs any longer then necessary as some instruments have difficultly in accurately counting small platelet analogs if the platelet gain settings are not calibrated correctly.

There is a correlation between the concentration of α-Naphthol used and the time required for heating (56° C.).

The increase in the concentration of α-Naphthol when used in conjunction with extensive heating at 56° C. improves the CV % of impedance and optical platelet counts. It also decreases the occurrence of PIC/POC flags.

Discussion:
The standard off-the-shelf platelet analogs (FIG. 2) are not completely being counted in the optical counting system of the newer technology instruments (CD4000 and CD Sapphire). This resulted in high imprecision when compared to the more reliable impedance counting method. The chemical 1-Napthol-3,6-Disulfonic Acid (hereafter designated as α-Naphthol) is used in the preparation of the platelet analogs, and depending on the water content of the raw material, the concentration to use may vary from lot to lot. Component manufacturing verifies the conductivity of each new lot of raw material received prior to producing a batch of platelet analogs. When the CD4000 is not able to accurately count all the particles in both the optical and impedance modes a system flag results; this is designated as a PIC/POC flag. This flag occurs when the delta difference between the two counting modes is greater than 20%.

Figure 4:
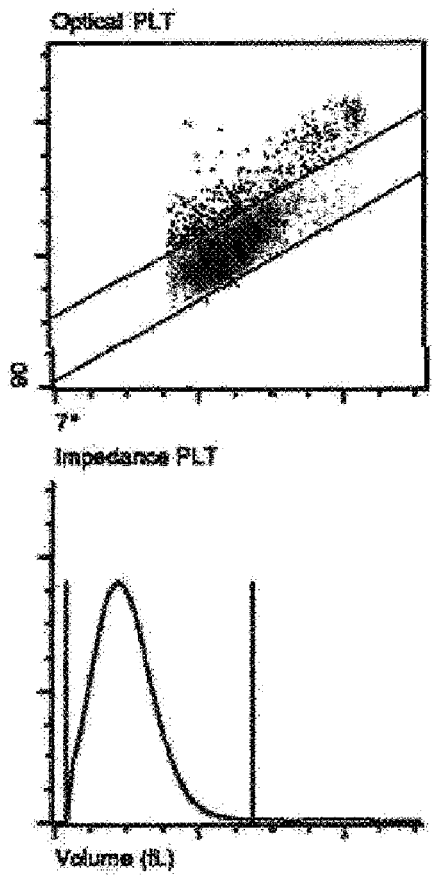
FIG. 4: analysis of platelet analog concentrate prepared with 210 g/L α-Naphthol (heated 2 days at 56° C., no glutaraldehyde) on an Abbott Cell-Dyn CD4000 hematology instrument.

The α-Naphthol plays a role in determining the size and shape based on electronic and optical detection properties of the finished analog. The experiment shows that increasing the concentration of α-Naphthol (from 210 g/L to 360 g/L) will improve the physical properties of the platelet analogs such that the CD4000 was able to accurately count all the particles in both the optical ($PLT_o$) and impedance ($PLT_i$) modes, after heating at 56° C. for two days (FIGS. 4 and 5).

Figure 5:
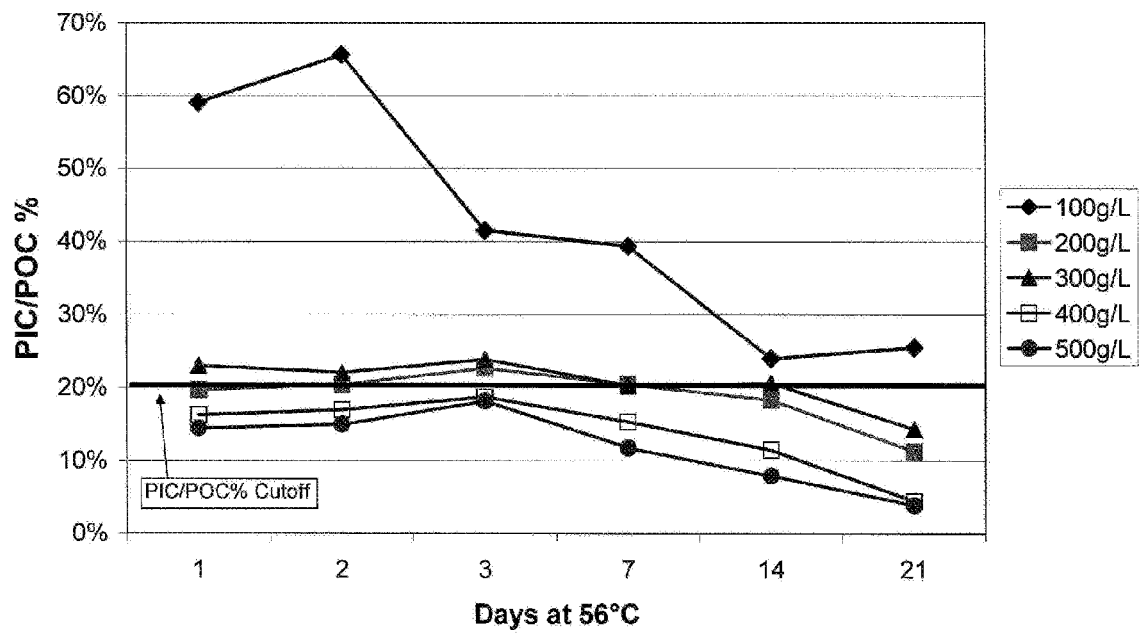
FIG. 5: effect of α-Naphthol (100-500 g/L) and heat-treatment (1-21 days at 56° C.) on PIC/POC %, analyzed on an Abbott Cell-Dyn CD400 hematology instrument.

The experiment showed that, by increasing the concentration of α-Naphthol (from 210 g/L to 500 g/L), the optical properties of the platelet analogs, after heating at 56° C. for three days, improved such that the CD4000 was able to accurately count all the particles in both the optical ($PLT_o$) and impedance ($PLT_i$) modes (FIG. 5). This experiment also indicated that there might be a correlation between the concentration of α-Naphthol and the time required, at 56° C.; to have the platelet analogs work properly on the CD4000.

Experiments showed that the longer the platelet analogs were heated, at 56° C., the smaller the MPV. Depending on the initial MPV there might be a maximum amount of time that the platelet analogs can be heated. As long as the MPV is within the specification range of 5-12 fL the platelet analogs can be heated until no PIC/POC flags occur on the CD4000.

This experiment showed the higher the concentration of α-Naphthol used, the better the optical properties of the platelets. As the heating time increased the number of PIC/POC flags decreased with an increasing α-Naphthol concentration. Thus, the heating is inversely related to the concentration of α-Naphthol.

Figure 6:
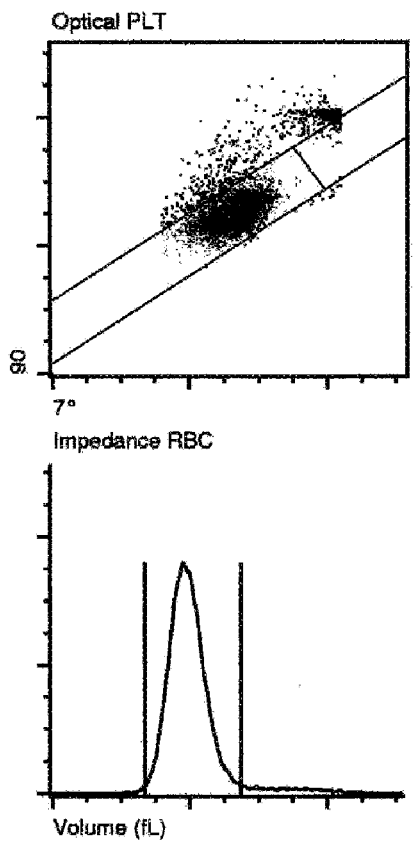
FIG. 6: analysis of platelet analog concentrate prepared with 450 g/L α-Naphthol (heated 3 days at 56° C., no glutaraldehyde) on an Abbott Cell-Dyn CD4000 hematology instrument.

To manufacture Platelet Analogs without PIC/POC flags, when run on the CD4000, a higher concentration of α-Naphthol (e.g., a minimum of 400 g/L) may be desirable. It should be noted that the concentration to be used may vary based on the quality of the raw material of α-Naphthol. When a new lot of raw material α-Naphthol is received an adjustment in the α-Naphthol concentration will need to be performed to optimize the concentration to use. A confirmatory batch of platelet analogs prepared with 450 g/L α-Naphthol and heated for 3 days at 56° C. is demonstrated in FIG. 6.

Heat the Platelet Analogs at 56° C. until no PIC/POC flags occur when run on the CD4000 at a normal count of 220×$10^3$-270×$10^3$.

All patents, patent applications, and other publications cited in this application, including published amino acid or polynucleotide sequences, are incorporated by reference in the entirety for all purposes.

What is claimed is:

1. A process for the manufacture of human platelet analogs for use as reference controls in automated blood cell analyzers, the process comprising the steps of:
   (a) shrinking red blood cells of a non-human vertebrate to the size of human platelets by extraction of cellular fluid from the red blood cells; and
   (b) heating the cells from step (a) at a temperature of at least 50° C. for a time period of at least 1 day, wherein the cells are treated with a denaturing agent prior to the heating or at the same time of the heating.

2. The process of claim 1, wherein step (a) further comprising heating the cells at a temperature of about 40° C. for about 0.5 to about 5 hours after the shrinking of the cells.

3. The process of claim 1, wherein step (a) further comprising heating the cells at a temperature of about 40° C. for about 3 hours after the shrinking of the cells.

4. The process of claim 1, wherein step (b) comprises treating the cells from step (a) with a denaturing agent for at least two hours and then removing the denaturing agent from the cells prior to the heating.

5. The process of claim 1, further comprising step (c) fixing the cells from step (b) with a fixing agent.

6. The process of claim 5, wherein the fixing agent is glutaraldehyde.

7. The process of claim 1, wherein the red blood cells are goat red blood cells.

8. The process of claim 1, wherein the heating in step (b) is performed at about 50° C. to about 75° C.

9. The process of claim 8, wherein the heating in step (b) is performed at about 56° C.

10. The process of claim 1, wherein the time period is at least 2 days.

11. The process of claim 1, wherein the time period is at least 3 days.

12. The process of claim 1, wherein the time period is at least 4 days.

13. The process of claim 1, wherein the time period is at least 7 days.

14. The process of claim 1, wherein the time period is at least 14 days.

15. The process of claim 1, wherein the time period is about 21 days.

16. The process of claim 1, wherein the denaturing agent is α-naphthol.

17. The process of claim 16, wherein α-naphthol concentration is 100 g/L to 500 g/L.

18. The process of claim 16, wherein α-naphthol concentration is at least 400 g/L.

19. The process of claim 16, wherein α-naphthol concentration is at least 500 g/L.

20. The process of claim 16, wherein the time period is at least 7 days and α-naphthol concentration is at least 400 g/L.

21. The process of claim 16, wherein the time period is at least 14 days and α-naphthol concentration is at least 400 g/L.

22. The process of claim 16, wherein the time period is at least 21 days and α-naphthol concentration is at least 400 g/L.

23. The process of claim 16, wherein the time period is about 21 days and α-naphthol concentration is about 500 g/L.

24. Modified red blood cells for use as reference controls in automated blood cell analyzers prepared by the process of claim 1.

* * * * *